(12) United States Patent
Deuel

(10) Patent No.: US 7,056,692 B2
(45) Date of Patent: Jun. 6, 2006

(54) MODULATION OF PLEIOTROPHIN SIGNALING BY RECEPTOR-TYPE PROTEIN TYROSINE PHOSPHATASE BETA/ZETA

(75) Inventor: Thomas Deuel, Cambridge, MA (US)

(73) Assignee: Barnes-Jewish Hospital, St. Louis, MO (US)

( * ) Notice: Subject to any disclaimer, the term of this patent is extended or adjusted under 35 U.S.C. 154(b) by 421 days.

(21) Appl. No.: 10/220,459

(22) PCT Filed: Feb. 28, 2001

(86) PCT No.: PCT/US01/06476

§ 371 (c)(1),
(2), (4) Date: Jan. 23, 2003

(87) PCT Pub. No.: WO01/64944

PCT Pub. Date: Sep. 7, 2001

(65) Prior Publication Data

US 2004/0014162 A1    Jan. 22, 2004

Related U.S. Application Data

(60) Provisional application No. 60/185,653, filed on Feb. 29, 2000.

(51) Int. Cl.
*C12Q 1/42*    (2006.01)
*C12N 9/12*    (2006.01)
*C12N 15/85*   (2006.01)

(52) U.S. Cl. .................... 435/21; 435/196; 435/320.1; 435/252.3; 536/23.2; 530/300

(58) Field of Classification Search .................. 435/21, 435/196, 320.1, 325; 536/23.2; 530/300
See application file for complete search history.

(56) References Cited

FOREIGN PATENT DOCUMENTS

WO        01/64944 A1      9/2001
WO        WO 01/96394 A2   12/2001

OTHER PUBLICATIONS

Zhang et al., "Human Breast Cancer Growth Inhibited in Vivo by a Dominant Negative Pleiotrophin Mutant," J. Biol. Chem., 1997, pp. 16733-16736, vol. 272.

Meng et al., "Pleiotrophin Signals Increased Tyrosine Phosphorylation of B-catenin Through Inactivation of the Intrinsic Catalytic Activity of the Receptor-Type Protein Tyrosine Phosphatase B/C," PNAS, 2000, pp. 2603-2608, vol. 97.

Maeda, Nobuaki, et al., A Receptor-like Protein-tyrosine Phosphatase PTPζRPTPβ Binds a Heparin-binding Growth Factor Midkine; The Journal of Biological Chemistry, Apr. 30, 1999, pp. 12474-12479, vol. 274, No. 18.

Maeda, Nobuaki, et al., 6B4 Proteoglycan/Phosphacan, an Extracellular Variant of Receptor-like Protein-tyrosine Phosphatase ζRPTPβ, Binds Pleiotrophin/Heparin-binding Growth-associated Molecule (HB-GAM), The Journal of Biological Chemistry, Aug. 30, 1996, pp. 21446-21452, vol. 271, No. 35.

Milev, Peter, et al., High Affinity Binding and Overlapping Localization of Neurocan and Phosphacan/Protein-tyrosine Phosphatase-ζ/β with Tenascin-R, Amphoterin, and the Heparin-binding Growth-associated Molecule, The Journal of Biological Chemistry, Mar. 20, 1998, pp. 6998-7005, vol. 273, No. 12.

Maeda, Nobuaki, et al., Involvement of Receptor-like Protein Tyrosine Phosphatase ζ/RPTPβ and its Ligand Pleiotrophin/Heparin-binding Growth-associated Molecule (HB-GAM) in Neuronal Migration, The Journal of Cell Biology, Jul. 13, 1998, pp. 203-216, vol. 142, No. 1.

Li, Yue-Sheng, et al., Pleiotrophin Stimulates Tyrosine Phosphorylation in NIH 3T3 and NB41A3 Cells, Biochemical and Biophysical Research Communications, Sep. 15, 1993, pp. 1089-1095, vol. 195, No. 2.

*Primary Examiner*—Tekchand Saidha
(74) *Attorney, Agent, or Firm*—Sonnenschein Nath & Rosenthal LLP

(57) ABSTRACT

The mechanism by which pleiotrophin binds to the receptor protein tyrosine phosphatase β/ζ(RPTP β/ζ) is disclosed along with methods of modulating both pleiotrophin expression and signaling to treat, prevent and inhibit abnormal cell growth states. Specifically provided are methods of inhibiting tumor growth, promotion, metastasis, invasiveness and angiogenesis as well as methods of preventing or inhibiting cell adhesion.

7 Claims, 4 Drawing Sheets

A.

0  2  4  8  10  15  20  0   min.

Anti-P-Tyr

Anti-β-catenin

B.

0   0.2   1   5   10   20   PTN-Fc ng/ml

Anti-P-Tyr

Anti-β-catenin

MODULATION OF PLEIOTROPHIN SIGNALING BY RECEPTOR-TYPE PROTEIN TYROSINE PHOSPHATASE BETA/ZETA

This application claims priority to copending U.S. provisional patent application Ser. No. 60/185,653, filed Feb. 29, 2000, incorporated herein by reference.

BACKGROUND OF THE INVENTION

Pleiotrophin (PTN) is a platelet-derived growth factor-inducible heparin-binding growth and differentiation factor that signals diverse phenotypes in normal and deregulated cellular growth and differentiation. See Milner, et al., (1989) *Biochem. Biophys. Res. Commun.* 165, 1096–1103; Rauvala, H. (1989) *EMBO J.* 8(10), 2933–2941; Li et al. (1990) *Science* 250, 1690–1694; Li et al., (1992) *Biochem. Biophys. Res. Commun.* 184: 427–432. PTN is nearly 50% identical with the retinoic acid-inducible factor midkine, which is also a growth and differentiation factor active in cultured fibroblasts, endothelial cells and epithelial cells. See Li et al., 1990, supra; Muramatsu et al.,(1993) *Dev. Biol.* 159, 392–402. Pleiotrophin gene expression is limited to specific cell types at different times during development; however, in adults, pleiotrophin gene expression is constitutive and limited to only a few cell populations except in sites of injury, when its expression is sharply increased. See Li et al. 1990, supra; Li et al., 1992 supra; Silos-Santiago et al, (1996) *J. Neurobiol.* 31, 283–296; Yeh et al., (1998) *J. Neurosci.* 18: 3699–3707.

The pleiotrophin (PTN) gene (Ptn) encodes an 18-kDa protein that is highly conserved among mammalian species and that functions as a weak mitogen and promotes neurite-outgrowth activity in vitro. Chauhan et al., *Proc. Nat'l. Acad. Sci.* 90: 679–682, 1993. PTN cDNA encodes a lysine-rich, highly basic protein of 168 amino acids with a 32-amino acid signal sequence that is highly conserved in bovine, rat, human, and chicken. Zhang et al. *J. Biol. Chem.* 272:16733–16736, 1997. The pleiotrophin gene is highly conserved among human, rat, bovine, and mouse species, and is developmentally regulated. Li et al., *Biochem. Biophys. Res. Common.* 184, 427–432, 1992. Li et al. (*Science* 250, 1690–1694, 1990) reported the isolation and sequence of the frill-length complementary DNA's (cDNA's) of the bovine, human, and rat genes of a heparin binding protein (i.e., pleiotrophin) with mitogenic activity toward rat and mouse fibroblasts. Comparison of predicted amino acid sequences of PTN from bovine, human, and rat revealed that PTN is conserved across the three species. Of 168 amino acid residues of PTN, 163 between bovine and human and 164 between rat and human are identical. The mature forms of bovine, human, and rat PTN exhibit overall 98 percent sequence similarity. Li et al., *Science* 250, 1690–1694, 1990. Zhang et al. describes the generation of a mouse PTN mutant gene construct containing sequences to encode mouse PTN residues −32 to +40 and a human wild type PTN expression vector containing a full-length human PTN cDNA fragment, and states that amino acid residues 1–40 (after cleavage of the signal peptide) of mouse and human PTN are identical, and thus the truncated PTN is equally effective in mouse and human lines. Zhang et al., *J. Biol. Chem.* 272: 16733–16736, 1997.

PTN also signals transformation; stable expression of an exogenous Ptn gene transforms NIH 3T3 cells and the Ptn-transformed NIH 3T3 cells form rapidly growing highly vascularized tumors in nude mice. Chauhan et al., (1993) *PNAS USA* 90: 679–682. Significantly, high level expression of the Ptn gene is found in many different human malignant tumors and in the cell lines that have been derived from these tumors; however, Ptn gene expression is not found in the normal cells from which the malignancy is derived. Fang, Hartmann et al. 1992, *J. Biol. Chem.* 267: 25889–97; Wellstein, Fang et al. 1992 *J. Biol. Chem.* 267: 2582–87; Tsutsui, Kadomatsu et al. 1993 *Cancer Res.* 53: 1281–85; Czubayko, Riegel et al. 1994, *J. Biol. Chem.* 269: 21358–63; Czubayko, Schulte et al. 1995, *Breast Cancer Res Treat* 36: 157–68; Czubayko, Schulte et al. 1996 *PNAS USA* 93: 14753–58; Brodeur, Nakagawara et al. 1997 *J. Neurooncol.* 31: 49–55; Zhang, Zhong et al. 1997 *J. Biol. Chem.* 272: 16733–36; Zhang and Deuel 1999 *Curr Opin Hematol* 6:44–50. Furthermore, high level expression of the Ptn gene may play a important role in developing a more aggressive phenotype in cancerous cells. Since it has also been shown that interruption of endogenous PTN signaling by a dominant negative PTN effector or a specific ribozyme reverses the malignant phenotype of human breast cancer cells (Zhang et al. 1997, J. Biol. Chem. 16733–36) and human melanoma cells (Czukayko et al., 1994 J. Biol. Chem. 269: 21358–63; Czubayko et al., 1996 PNAS USA 93: 14753–58), acquisition of PTN signaling during the course of these malignancies may trigger a more aggressive phenotype.

It is known that cells rely, to a great extent, on extracellular molecules as a means by which to receive stimuli from their immediate environment. These extracellular signals are important in the regulation of diverse cellular processes such as differentiation, contractility, secretion, cell division, cell migration, contact inhibition and metabolism. The extracellular molecules include, for example, hormones, growth factors or neurotransmitters, which may function as ligands that bind specific cell surface receptors. The binding of these ligands to their receptors triggers signal transduction, a cascade of reactions that brings about both the amplification of the original stimulus and the coordinate regulation of the separate cellular processes mentioned above.

A central feature of signal transduction is the reversible phosphorylation of certain proteins. The phosphorylation or dephosphorylation of certain amino acid residues may trigger conformational changes in regulated proteins which results in the alteration of their biological properties. Proteins are phosphorylated by protein kinases and are dephosphorylated by protein phosphatases. Phosphorylation is a dynamic process involving competing phosphorylation and dephosphorylation reactions, and the level of phosphorylation at any given instant reflects the relative activities, at that particular instant, of the protein linases and phosphatases that catalyze these reactions.

Protein kinases and phosphatases are classified according to the amino acid residues they act on, for example, the class of tyrosine kinases and phosphatases act on tyrosine residues. See Fischer, E. H. et al., (1991) *Science* 253: 401–406; Schlessinger, J. and Ullrich, A., (1992) *Neuron* 9:383–391; Ullrich, A. and Schlessinger, J., (1990) *Cell* 61:203–212. Protein kinases and phosphatases may further be defined as being receptors, i.e., the enzymes are an integral part of a transmembrane, ligand-binding molecule, or as non-receptors, meaning they respond to an extracellular molecule indirectly by being acted upon by a ligand-bound receptor.

The receptor class of protein tyrosine phosphatases (PTPs) is made up of high molecular weight, receptor-linked PTPases, termed RPTPases. Structurally resembling growth factor receptors, RPTPases consist of an extracellular, putative ligand-binding domain, a single transmembrane segment, and an intracellular catalytic domain (reviewed in Fischer et al., (1991) *Science* 253:401–406). Since the initial purification, sequencing and cloning of a protein tyrosine phosphatase (Thomas, M. L. et al., (1985) *Cell* 41:83), additional potential protein tyrosine phosphatases have been identified. One such example is a proteoglycan-type protein tyrosine phosphatase, named protein tyrosine phosphatase ζ/receptor-like PTP β (RPTP β/ζ). Recently, PTN was found to interact with the transmembrane RPTP β/ζ. See Maeda et al., (1996) *J. Biol. Chem.* 271: 21446–21452: Maeda, N. & Noda, M. (1998) *J. Cell Biol.* 142, 203–216; Milev et al., (1998) *J. Biol. Chem.* 273: 6998–7005.

The PTN gene is a protooncogene and is expressed in many human tumors such as breast cancer, neuroblastoma, glioblastoma, prostate cancer, lung cancer and Wilms' tumor and cell lines derived from human tumors. See Fang et al., (1992) *J. Biol. Chem.* 267: 25889–25897; Chauhan et al, (1993) *Proc. Natl. Acad. Sci. USA* 90: 679–682; Wellstein et al., (1992) *J. Biol. Chem.* 267: 2582–2587; Tsutsui et al., (1993) *Cancer Res.* 53:1281–1285; Nakagawara et al., (1995) *Cancer Res.* 55: 1792–1797. The importance of PTN in malignant cell growth was first established when introduction of the exogenous Ptn gene into NIH 3T3 cells and NRK cells led to morphological transformation, anchorage independent growth and tumor formation with significant neovascularization in vivo in the nude mouse. See Chauhan et al., 1993 *PNAS USA* 90: 679–82. It was subsequently shown that SW13 cells transformed by pleiotrophin also develop highly vascular tumors in the flanks of athymic nude mice. See Fang et al., 1992 *J. Biol. Chem.* 267: 258889–97. Further, interruption of PTN signaling has resulted in the reversal of the transformed phenotype of human breast cancer cells that constitutively express the PTN gene (Zhang et al., (1997) *J. Biol. Chem.* 272: 16733–16736) and effectively reverted the malignant phenotype of cultured human melanoma cells (Czubayko et al, (1994) *J. Biol. Chem.* 269: 21358–21363). It is believed that expression of the Ptn gene and its signaling pathway play a crucial regulatory role in many neoplasms of diverse origins. Thus, identification of the molecules and mechanisms of the PTN signaling pathway that are specific and crucial for tumor proliferation, angiogenesis and invasiveness would allow for the development of clinical applications and specific anti-tumor drugs to treat cancer. As such, a need presently exists for the identification of compounds or agents that disrupt or interfere with PTN signaling in order to influence malignant transformation and inhibit tumor growth and angiogenesis.

Further, PTN also induces neurite outgrowth from neurons (Rauvala 1989, supra; Li et al. 1990, supra) and glial process outgrowth from glial progenitor cells, suggesting that Ptn gene expression may influence a very broad range of functional activities. Since the pleiotrophin gene expression is upregulated by PDGF, PTN may act downstream of PDGF to mediate aspects of the PDGF signal. Thus, the activation of their respective signaling pathways is critical to the temporal maturation of oligodendrocyte progenitors and the properties of PTN suggest that PTN is ideally positioned to signal activation of genes important in maturation of glial elements at this critical time of development. As differentiation of oligodendrocytes is required for myelination of nerve fibers and consequently, important to nerve conduction, the determination of mechanisms for modulating PTN signaling during the differentiation of oligodendrocytes would be desirable. Accordingly, a need presently exists to determine the mechanism and molecules by which PTN signals in order to develop methods to treat and prevent nerve injury and demyelinating diseases.

While the molecules through which PTN signals have not to date been established, in addition to interacting with RPTP β/ζ, PTN has also been shown to bind to heparin, heparin sulfate proteoglycans and extracellular matrix. See Milner et al. 1989, supra; Rauvala, 1989 supra; Li et al., 1990, supra; Raulo et al., (1994) *J. Biol. Chem.* 269: 12999–13004; Maeda et al., (1996) *J. Biol. Chem.* 271: 21446–21452; Kinnunen et al., (1996) *J. Biol. Chem.* 271: 2243–2248. In addition to interacting with RPTP β/ζ, PTN induces tyrosine phosphorylation of a 190 kDa protein in PTN treated murine fibroblasts. See Li, Y. S. & Deuel, T. F. (1993) *Biochem. Biophys. Res. Commun.* 195: 1089–1095.

Thus, the interruption of PTN signaling impacts the events downstream in the signaling cascade such as cell proliferation and differentiation. Accordingly, there is presently a need to understand PTN signaling and the interaction between RPTP β/ζ and PTN in order to modulate the PTN signaling pathway to produce increased or decreased PTN activity in order to define compounds which useful in therapy and treating disease influenced by the expression of pleiotrophin such as cancer.

SUMMARY OF THE INVENTION

Applicants have shown that receptor protein tyrosine phosphatase β/ζ (RPTP β/ζ) is the receptor for pleiotrophin (PTN). Binding of RPTP β/ζ and PTN inhibits RPTP β/ζ enzymatic activity and results in higher levels of tyrosine phosphorylation of β-catenin. Further, binding of RPTP β/ζ and PTN also reduces the levels of the β-catenin interaction with E-cadherin and thus affects the potential for cells to adhere with each other.

The elucidation of this relationship between RPTP β/ζ and PTN can be used to define compounds which useful in therapy and treating disease. For example, this pathway can be modulated to mimic increased PTN activity in order to promote glial process formation, neuron growth and differentiation, endothelial cell growth and differentiation, and fibroblast growth. The method of accomplishing these effects involves the use of agents which either (a) mimic PTN binding to RPTP β/ζ, (b) inhibit the binding of RPTP β/ζ to B-catenin, (c) enhance or increase the binding or the amounts of phosphorylated β-catenin to LEF-1 to form a transcription factor, or (d) mimic PTN binding to RPTP β/ζ.

Thus, among the several aspect of the present invention, therefore, include methods of monitoring levels of tyrosine phosphatase activity of RPTP β/ζ in a cell or tissue comprising contacting the cell or tissue with an effective amount of pleiotrophin which binds to the active site of RPTP β/ζ thereby reducing tyrosine phosphatase activity of RPTP β/ζ. Preferably, the administration of pleiotrophin results in the increase of PTN activity and the reduction of tyrosine phosphatase activity of RPTP β/ζ. Furthermore, the binding of pleiotrophin to the active site of RPTP β/ζ preferably results in ligand-dependent dimerization of RPTP β/ζ and inactivates the catalytic activity of RPTP β/ζ.

Another aspect of the present invention is directed to methods of regulating levels of tyrosine phosphatase activity of protein tyrosine phosphataseζ/receptor-like protein tyrosine phosphatase β (RPTP β/ζ) in a cell or tissue, the method comprising:

a. determining whether the tyrosine phosphatase activity should be reduced or increased in the cell or tissue to effectuate a desired physiologic change;

b. administering an effective amount of pleiotrophin, pleiotrophin inhibitor or mimic to reduce or increase the tyrosine phosphatase activity of RPTP β/ζ;

c. monitoring the cell or tissue for the appearance of the desired physiologic change; and d. determining whether to further modify levels of tyrosine phosphatase activity.

Yet another aspect of the present invention is directed to methods of increasing tyrosine phosphorylation of β-catenin in a cell or tissue comprising contacting the cell or tissue that expresses RPTP β/ζ with an effective amount of pleiotrophin thereby reducing tyrosine phosphatase activity of RPTP β/ζ and increasing tyrosine phosphorylation of β-catenin.

In another aspect, methods for modulating cell-cell adhesion are provided which include contacting a cell with pleiotrophin in an amount sufficient to inactivate tyrosine phosphatase activity of RPTP β/ζ thereby increasing tyrosine phosphorylation of β-catenin in the cell and decreasing interaction of β-catenin and E-cadherin.

The PTN signaling pathway can also be modulated to mimic reduced PTN activity to prevent or inhibit the growth or promotion of tumor cells and the loss of cell-cell interactions in cancer. This could be accomplished by agents that (a) reduce or block PTN binding to RPTP β/ζ, (b) ensure the binding of RPTP β/ζ to β-catenin and its ability to maintain normal steady state levels of tyrosine phophorylation of β-catenin, (c) reduce or eliminate the binding of phosphorylated β-catenin to LEF-1 to form a transcription factor, or (d) reduce or eliminate the translocation of phosphorylated β-catenin to the nucleus. Agents with these activities can be identified by screening chemical libraries in in vitro assays as described in the Examples herein.

Thus, another aspect of the present invention is directed to methods of inhibiting tumor invasiveness in a tissue comprising contacting the tissue with an effective amount of a compound which binds to RPTP β/ζ or pleiotrophin thereby preventing pleiotrophin from binding to RPTP β/ζ and decreasing tyrosine phosphatase activity of RPTP β/ζ.

Relatedly, the invention is further directed to methods of inhibiting metastasis of a tumor comprising contacting the tumor with an effective amount of a compound which binds to pleiotrophin or RPTP β/ζ in the tissue thereby preventing pleiotrophin from binding to RPTP β/ζ and increasing tyrosine phosphatase activity of RPTP β/ζ.

Yet another method of inhibiting tumor angiogenesis, progression or promotion includes reducing the level of PTN signaling through RPTP β/ζ in the tumor cells.

Further, methods of inhibiting tumor growth in a mammal include administering to the mammal an effective amount of a compound which binds to pleiotrophin or RPTP β/ζ thereby reducing the level of pleiotrophin signaling through RPTP β/ζ in the tumor cells.

Also provided are pleiotrophin mimics which are compounds which bind to pleiotrophin or RPTP β/ζ in manner which corresponds to the effective binding of PTN to RPTP β/ζ in a cell or tissue.

Other aspects and features will be in part apparent and in part pointed out hereinafter.

BRIEF DESCRIPTION OF THE DRAWINGS

FIG. 1A shows lysates of U373-MG glioblastoma cells immunoprecipitated with anti-RPTP β/ζ monoclonal antibodies. The immunoprecipitates were separated on 6% acrylamide gel, transferred to a poly(vinylidene difluoride) membrane, and probed with anti-RPTP β/ζ antibodies. The arrowheads indicate the RPTP β/ζ-spliced products of ≈230, 130 and 85 kDa. FIG. 1B shows Western analysis of RPTP β/ζ captured by PTN-Fc. Lysates of U373-MG cells were incubated with PTN-Fc and proteins interactive with PTN-Fc (right lane) were captured with Protein A Sepharose-4B beads for 2 hours. The beads were washed in cold lysis buffer, boiled in SDS/PAGE sample buffer, and the eluted proteins were separated on an 8% acrylamide gel and analyzed by Western blots probed with anti-RPTP β/ζ monoclonal antibodies. As a control, PTN-Fc was replaced with an equal amount of human IgG (left lane). The arrowheads indicate the ≈130 and ≈85 kDa-spliced products of RPTP β/ζ. FIG. 1C shows western analysis of RPTP β/ζ captured by endogenous PTN. Lysates of U373-MG cells were incubated with anti-PTN monoclonal antibodies (right lane) and the complexes were captured with Protein A Sepharose-4B beads for 2 hours. The beads were washed in cold lysis buffers, boiled in SDS-PAGE sample buffer, and the eluted proteins were separated on an 8% acrylamide gel and analyzed by Wester blots probes with anti-RPTP β/ζ monoclonal antibodies. As a control, mouse IgG replaced the anti-PTN antibody (left lane). The arrowheads indicate the 130 and =85 kDa-spliced products of RPTP β/ζ.

FIG. 2A shows inhibition of the endogenous RPTP β/ζ tyrosine phosphatase activity in PTN-treated U373-MG cells. The left bar represents tyrosine phosphatase activity in immunoprecipitates from lysates of untreated cells with mouse IgG (control) to replace the anti-RPTP β/ζ antibodies. The center bar represents tyrosine phosphatase activity in immunoprecipitates with anti-RPTP β/ζ antibodies from lysates of untreated cells, and the right bar represents tyrosine phosphatase activity of immunoprecipitates with anti-RPTP β/ζ antibodies from lysates of cells treated with recombinant PTN (50 ng/ml). FIG. 2B shows inhibition of recombinant RPTP β/ζ phasphatase activity in Sf9 cell membranes. The right two bars show membrane fractions of Sf9 cells that were infected by a baculovirus containing a cDNA-encoding RPTP β/ζ, or were uninfected (left two bars) that were untreated (−PTN) or treated (+PTN) with 50 ng/ml PTN. FIG. 2C shows a time course of PTN-dependent inactivation of RPTP β/ζ in PTN-treated (50 ng/ml) Sf9 cell membranes expressing RPTP β/ζ (solid bars) and SF9 cell membranes without RPTP β/ζ (open bar, t=0 only).

FIG. 3A shows that PTN-Fc is in complex with RPTP β/ζ and β-catenin. PTN-Fc treated confluent U373-MG cells from 60-mm dish were chemically cross-linked with 3,3'dithiobis sulfosuccinmidyl propionate. Lysates from PTN-Fc-treated, chemically cross-linked cells (lanes 1) or Fc-(alone) treated (control) U373-MG cells (lane 2) were incubated with Protein A Sepharose, washed, eluted with SDS sample buffer with 5% 2-mercaptoethanol, and analyzed in 6% SDS gels and Western blots. Lysates from untreated U373-MG cells alone (lane 3) were also analyzed as a control. Western blots were analyzed with anti-β-catenin (right) or anti-RPTP β/ζ antibodies (left). Arrowheads identify RPTP β/ζ-spliced products of =250, 230, 180 and 85 kDa (left) and β-catenin (94 kDa) (right). FIG. 2B shows that β-catenin interacts with proximal (catalytic) domain of RPTP β/ζ. The GST-D1-RPTP β/ζ wild-type, GST-D1-Cys-1925-Ser (inactivating) mutant fusion protein or GST alone were expressed and immobilized with glutathione-Sepharose-48 beads, incubated with U373-MG cell lysates, washed, and analyzed in Western analysis with the a-phosphotyrosine antibodies and visualized with the enhanced chemiluminescence ECL-PLUS system (lower). The same blot was reprobed with α-β-catenin antibodies and detected as above (upper).

FIG. 4A is a time course of the tyrosine phosphorylation of β-catenin in response to PTN-FC treatment. Cells were treated with 10 ng/ml PTN-Fc for the times indicated. Lysates were immunoprecipitated with α-β-catenin antibodies and analyzed in Western blots probed with α-phosphotyrosine anti9bodies (upper) and the blots were reprobed with α-β-catenin antibodies and (lower). In FIG. 4B, U373-MG cells were treated with different doses of PTN-Fc for 20 minutes. Cells were grown to near confluence, and then were serum-starved for 48 hours. PTN-FC was added up to the indicated concentrations. The Fc fragment alone (20 ng/ml) was added as a control. Lysates were immunoprecipitated and analyzed in Western blots with antiphosphotyrosine antibodies as described above. Parallel immunoblots were probed for β-catenin.

DETAILED DESCRIPTION OF THE INVENTION

Figure 1:
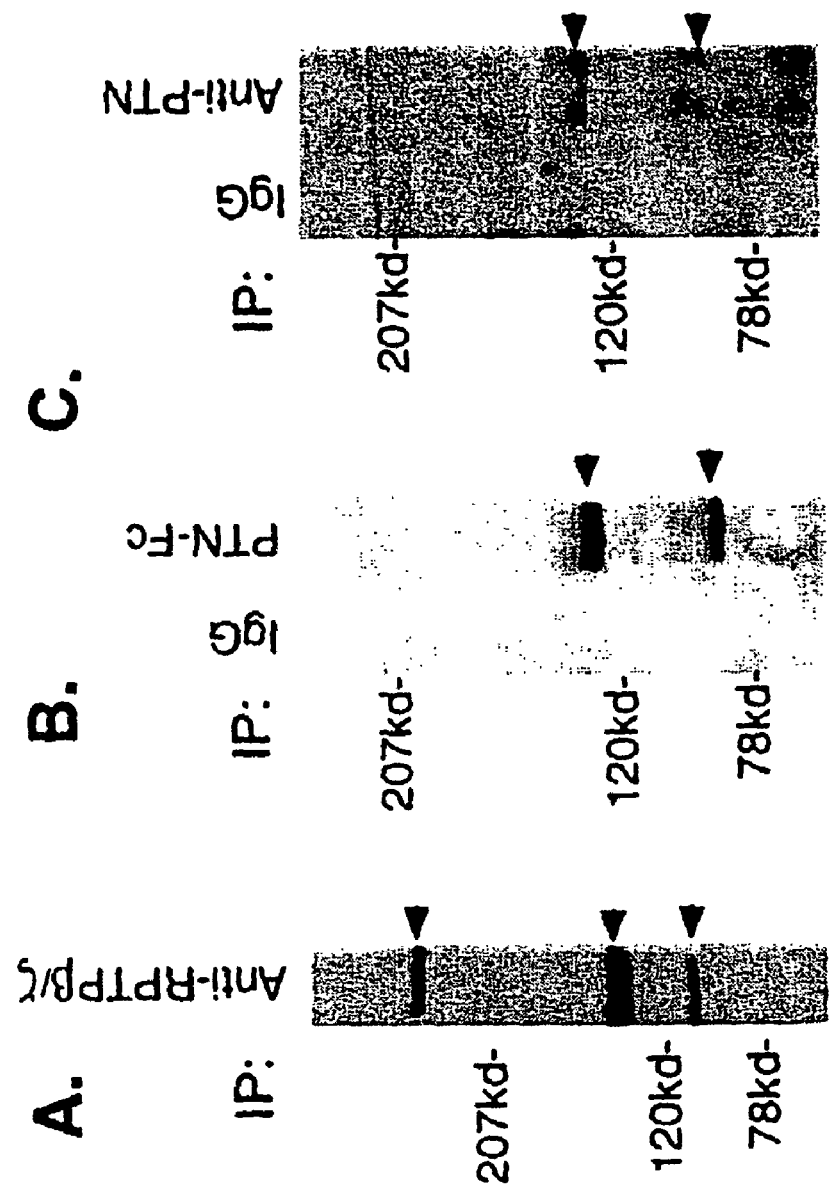
FIGS. 1A, 1B and 1C are a set of three western blots showing the association of RPTP β/ζ with PTN.

The following detailed description is provided to aid those skilled in the art in practicing the present invention. Even so, this detailed description should not be construed to unduly limit the present invention as modifications and variations in the embodiments discussed herein can be made by those of ordinary skill in the art without departing from the spirit or scope of the present inventive discovery.

All publications, patents, patent applications, databases and other references cited in this application are herein incorporated by reference in their entirety as if each individual publication, patent, patent application, database or other reference were specifically and individually indicated to be incorporated by reference.

Abbreviations and Definitions

As used herein, "Ptn" refers to the pleiotrophin gene.

As used herein, PTN refers to the pleiotrohin protein.

The phrase "preventing or inhibiting interaction between RPTP β/ζ and PTN" indicates that the normal interaction between a RPTP β/ζ and PTN is being affected either by being inhibited or reduced to such an extent that the binding of PTN to RPTP β/ζ is measurably lower than is the case when PTN is interacting with RPTP β/ζ at conditions which are substantially identical (with regard to pH, concentration of ions, and other molecules) to the native conditions in the cell or tissue.

By the phrase "effective amount" is meant the amount of a desired compound necessary to (a) inhibit PTN binding to RPTP β/ζ and inhibits its intrinsic catalytic activity, (b) inhibit the binding of RPTP β/ζ to β-catenin, (c) inhibit the binding of phosphorylated β-catenin to LEF-1 to form a transcription factor, or (d) mimic PTN binding to RPTP β/ζ.

By the term "a mimic of PTN" denotes any substance which mimics or has the ability to bind to pleiotrophin or to RPTP β/ζ in a manner which prevents the effective binding of PTN to RPTP β/ζ in a cell or tissue. Such a mimic of PTN can be a modified form of the intact PTN or it can be a modified form of the protein which may be coupled to a probe, marker or another moiety. Another such mimic can be obtained by modifying or mutating PTN so that it differs from the wild-type sequence encoding PTN by the substitution of at least one amino acid residue of the wild-type sequence with a different amino acid residue and/or by the addition and/or deletion of one or more amino acid residues to or from the wild-type sequence. The additions and/or deletions can be from an internal region of the wild-type sequence and/or at either or both of the N- or C-termini. In the present context, PTN and mimics thereof exhibit at least one binding characteristic relevant for the interaction of PTN and RPTP β/ζ during PTN signaling in a cell or tissue. Such mimics and compounds can also be small molecules which have the effects of the mimicking factor described above.

The term "ligand-dependent receptor inactivation of RPTP β/ζ" refers to the mechanism in PTN signaling pathways by which PTN binds to RPTP β/ζ, inactivates the catalytic tyrosine phosphatase activity of RPTP β/ζ and disrupts the normal role of RPTP β/ζ in the regulation of steady-state tyrosine phosphorylation of downstream signaling molecules.

In accordance with the present invention, applicant has identified that PTN is a natural ligand for RPTP β/ζ. PTN is the first natural ligand identified for any of the RPTP family and its identification provides a unique tool to pursue both the novel signaling pathway activated by PTN and the relationship of PTN signaling with other pathways regulating β-catenin. Furthermore, the finding of RPTP β/ζ as the functional receptor for PTN is particularly interesting because to date, there are no known soluble ligands for this class of transmembrane receptor tyrosine phosphatases and thus, PTN may be a unique probe for exploring the receptor class of transmembrane tyrosine phosphatases and how they signal.

Without intending to be bound by any particular theory, it is believed that PTN signals through "ligand-dependent receptor inactivation" of RPTP β/ζ and disrupts its normal roles in the regulation of steady-state tyrosine phosphorylation of downstream signaling molecules. Specifically, PTN binds to RPTP β/ζ, inducing ligand-dependent dimerization of RPTP β/ζ and functionally inactivates the catalytic tyrosine phosphatase activity of RPTP β/ζ, presumably denying the access of substrate(s) to its catalytic site. An active site-containing domain of RPTP β/ζ both binds β-catenin and functionally reduces its levels of tyrosine phosphorylation when added to lysates of pervanidate-treated cells. Thus, this mechanism of PTN signaling through RPTP β/ζ provides further insight into the mechanism by which PTN affect downstream signaling.

Further, β-catenin interacts with the catalytically active D1 domain of RPTP β/ζ and addition of the D1 domain of RPTP β/ζ with an active tyrosine phosphatase catalytic site to lysates of cells previously treated with pervanidate sharply reduces levels of tyrosine phosphorylation of β-catenin; it is believed that β-catenin is a substrate for the tyrosine phosphatase activity of RPTP β/ζ. Furthermore, because PTN rapidly signals tyrosine phosphorylation of β-catenin in intact U373-MG cells, inactivation of RPTP β/ζ is believed to be directly responsible for the increase in tyrosine phosphorylation of β-catenin as a result of the disruption of the normal balance of tyrosine kinase and phosphatase activities. Thus, RPTP β/ζ is intrinsically active and a principal regulator of tyrosine phosphorylation levels of β-catenin. In PTN-stimulated cells, RPTP β/ζ is believed to be functionally inactivated, steady-state levels of β-catenin tyrosine phosphorylation and other downstream signaling molecules are increased and a PTN-dependent downstream signaling cascade is initiated. Thus, β-catenin not only is an endogenous substrate for RPTP β/ζ, but also a downstream mediator of PTN signaling.

Accordingly, the elucidation of this relationship between RPTP β/ζ and PTN can be used to define compounds which useful in therapy and treating disease. For example, this pathway can be modulated to mimic increased PTN activity in order to promote glial process formation, neuron growth and differentiation, endothelial cell growth and differentiation, and fibroblast growth. The method of accomplishing these effects involves the use of agents which either (a) mimic PTN binding to RPTP β/ζ, (b) inhibit the binding of RPTP β/ζ to β-catenin, (c) enhance or increase the binding or the amounts of phosphorylated β-catenin to LEF-1 to form a transcription factor, or (d) mimic PTN binding to RPTP β/ζ.

Thus, one aspect of the present invention provides methods of regulating and/or modifying levels of tyrosine phosphatase activity of RPTP β/ζ in a cell or a tissue. Such methods include determining whether the tyrosine phosphatase activity should be reduced or increased in the cell or tissue to effectuate a desired physiologic change; administering an effective amount of pleiotrophin, pleiotrophin inhibitor or pleiotrophin mimic to reduce or increase the tyrosine phosphatase activity of RPTP β/ζ; monitoring the cell or tissue for the appearance of the desired physiologic change; and determining whether to further modify levels of tyrosine phosphatase activity. Such desired physiological changes include but are not limited to tumor promotion, growth angiogenesis, metastasis, modulation of cell-cell adhesion and differentiation of oligodendrocytes.

In another embodiment, the present invention provides methods for monitoring tyrosine phosphatase activity of RPTP β/ζ in a cell or tissue. This method involves contacting the cell or tissue with an effective amount of pleiotrophin which binds to RPTP β/ζ, preferably the active site of RPTP β/ζ. Preferably, in cells which express PTN, administering pleiotrophin results in the reduction of tyrosine phosphatase activity of RPTP β/ζ. Furthermore, the binding of pleiotrophin to the active site of RPTP β/ζ preferably results in ligand-dependent dimerization of RPTP β/ζ and inactivates the catalytic activity of RPTP β/ζ.

Further, an (inactivating) active-site mutant of RPTP β/ζ also binds β-catenin but fails to reduce tyrosine phosphorylation of β-catenin. In parallel to its ability to inactivate endogenous RPTP β/ζ, PTN increases tyrosine phosphorylation of β-catenin in PTN-treated cells. Thus, in unstimulated cells, RPTP β/ζ is intrinsically active and functions as an important regulator in the reciprocal control of the steady state tyrosine phosphorylation levels of β-catenin by tyrosine kinases and phosphatases. As such, it is believed that RPTP β/ζ is a functional receptor for PTN and that PTN signals through ligand-dependent receptor inactivation of RPTP β/ζ to increase levels of tyrosine phosphorylation of β-catenin to initiate downstream signaling.

Formation of cell-cell adhesion requires members of the cadherin-catenin families to link the highly conserved cadherin cytoplasmic domain to the actin-based cytoskeleton and to connect adjacent cells via the cadherin extracellular domains. See Kypta et al., (1996) *J. Cell Biol.* 134: 1519–1529; Tonks, N. K. & Neel, B. G. (1996) *Cell* 87: 365–368; Miller, J. R., & Moon, R. T. (1996) *Genes Dev.* 10, 2527–2537. Balsamo et al. (*J. Cell. Biol.* 134: 801–813 (1996)) demonstrated that the association of β-catenin with E-cadherin is inversely related to tyrosine phosphorylation levels of β-catenin in pervanidate-treated cells, raising the distinct possibility that through its ability to increase tyrosine phosphorylation of β-catenin, PTN disrupts the normal association of β-catenin and E-cadherin, underscoring the need for reciprocal control of tyrosine phosphorylation of β-catenin. Kypta et al.,(1996) *J. Cell Biol.* 134: 1519–1529; Hoschuetzky et al.,(1994) *J. Cell Biol.* 127: 1375–1380; Fischer et al.,(1991) *Science* 253: 401–406; Brady-Kalnay et al.,(1995) *J. Cell. Biol.* 130: 977–986; Brady-Kalnay et al., (1998) *J. Cell. Biol.* 141: 287–296. Because constitutive expression of PTN itself transforms cells with striking loss of contact inhibition, cell adhesion, and striking disruption of cytoskeletal architecture, it is believed that the ability of PTN to disrupt the reciprocal control of tyrosine phosphorylation of β-catenin by tyrosine kinases and phosphatases may account for many of the properties of PTN-transformed cells and those human cancer cells which constitutively express PTN.

Thus, in a preferred embodiment of the invention, tyrosine phosphorlyation of β-catenin a cell or tissue is increased, preferably in tissues or cells that express PTN. Preferably, increasing levels of tyrosine phosphorlyation of β-catenin in a cell or tissue reduces the level of β-catenin interaction with E-cadherin thus affecting cell-cell adhesion. Loss of cell-cell interactions in cancer have a profound effect on tumor formation, promotion, angiogenesis and metastatsis. Preferably, increasing the levels of tyrosine phosphorlyation of β-catenin in a cell or tissue reduces the level of β-catenin interaction with E-cadherin and more preferably, affects the potential for cells to adhere with each other. Hence, in a preferred embodiment, methods of increasing the levels of tyrosine phosphorlyation of β-catenin in a cell or tissue by administering pleiotrophin will affect cell-cell adhesion, preferably, by increasing the levels of tyrosine phosphorlyation of β-catenin to prevent or inhibit cell-cell adhesion. These methods involve contacting the cell or tissue with an effective amount of pleiotrophin thereby reducing tyrosine phosphatase activity of RPTP β/ζ and increasing tyrosine phosphorylation of β-catenin. Preferably, pleiotrophin inactivates tyrosine phosphatase activity of RPTP β/ζ by binding to the active site of RPTP β/ζ and more preferably, induces ligand-dependent dimerization of RPTP β/ζ. In a preferred embodiment, the ligand-dependent dimerization of RPTP β/ζ inhibits the ability of β-catenin to bind to the catalytic site of RPTP β/ζ, preferably the D1 site of RPTP β/ζ.

In another aspect of the invention, the PTN signaling pathway can be modulated to mimic reduced PTN activity thereby impacting events downstream in the signaling cascade such as inhibiting the growth, proliferation, promotion, angiogenesis and/or metastatsis of tumor cells and the loss of cell-cell interactions in cancer. This can be accomplished by agents that (a) reduce or block PTN binding to RPTP β/ζ, (b) ensure the binding of RPTP β/ζ to β-catenin and its ability to maintain normal steady state levels of tyrosine phophorylation of β-catenin, (c) reduce or eliminate the binding of phosphorylated β-catenin to LEF-1 to form a transcription factor, or (d) reduce or eliminate the translocation of phosphorylated β-catenin to the nucleus. Further, it is believed that PTN also signals nuclear translocation and transactivation of genes signaling oncogenic pathways as a consequence of the release of β-catenin from E-cadherin. Desirable results of decreasing PTN signaling is the reduction or inhibition of tumor growth, promotion, proliferation, angiogenesis and metastasis. During the study of PTN signaling, Applicant observed that PTN not only transformed NIH 3T3 cells but that NIH-PTN cells established rapidly growing highly vascularized tumors in nude mice, suggesting that PTN may promote tumor growth by inducing tumor angiogenesis. Subsequently, it was shown that introduction of PTN into human adrenal carcinoma cells increased the number of new blood vessels when these cells were implanted into the flanks of nude mice. Furthermore, it was also possible to show that the stimulation of angiogenesis in SW13 cells by constitutive expression of Ptn could be localized to a domain of PTN within PTN amino acid residues 69–136.

Accordingly in a preferred embodiment of the invention, methods of inhibiting tumor invasiveness in a tissue the method include contacting the tissue with an effective amount of a compound which binds to RPTP β/ζ or pleiotrophin thereby preventing pleiotrophin from binding to RPTP β/ζ and decreasing tyrosine phosphatase activity of RPTP β/ζ.

In another embodiment, methods are provided which reduce the level of PTN signaling through RPTP β/ζ in the tumor cells thus resulting in the inhibition of tumor angiogenesis, progression or promotion.

Yet another embodiment provides a method of inhibiting tumor growth in a mammal comprising administering to the mammal an effective amount of a compound which binds to pleiotrophin or RPTP β/ζ thereby reducing the level of pleiotrophin signaling through RPTP β/ζ in the tumor cells. Preferably, the tumor cells are tumor cells from breast cancer, neuroblastoma, glioblastoma, prostate cancer, lung cancer and Wilms' tumor.

In the above methods, an effective amount of a compound which binds to RPTP β/ζ or pleiotrophin can be antibodies to RPTP β/ζ, antibodies to pleiotrophin or a pleiotrophin mimic. Accordingly, in one aspect, the present invention directed to a compound, preferably a pleiotrophin mimic, which will mimic the capability of pleiotrophin to bind to RPTP β/ζ, thereby modulating, disrupting or interfering with PTN signaling. The compound can be any compound, preferably a peptide, which will bind to pleiotrophin or RPTP β/ζ and prevent the binding of pleiotrophin to RPTP β/ζ. In a preferred embodiment, the pleiotrophin mimic is a peptide compound. It will be appreciated that by virtue of the present invention, the polypeptide pleiotrophin mimic can be synthesized using conventional synthesis procedures commonly used by one skilled in the art. For example, the polypeptides can be chemically synthesized using an automated peptide synthesizer (such as one manufactured by Pharmacia LKB Biotechnology Co., LKB Biolynk 4170 or Milligen, Model 9050 (Milligen, Millford, Mass.)) following the method of Sheppard, et al., Journal of Chemical Society Perkin I, p. 538 (1981). In this procedure, N,N'-dicyclohexylcarbodiimide is added to amino acids whose amine functional groups are protected by 9-flourenyl-methoxycarbonyl (Fmoc) groups and anhydrides of the desired amino acids are produced. These Fmoc-amino acid anhydrides can then be used for peptide synthesis. A Fmoc-amino acid anhydride corresponding to the C-terminal amino acid residue is fixed to Ultrosyn A resin through the carboxyl group using dimethylaminopyridine as a catalyst. Next, the resin is washed with dimethylformamide containing piperidine, and the protecting group of the amino functional group of the C-terminal acid is removed. The next amino acid corresponding to the desired peptide is coupled to the C-terminal amino acid. The deprotecting process is then repeated. Successive desired amino acids are fixed in the same manner until the peptide chain of the desired sequence is formed. The protective groups other than the acetoamidomethyl are then removed and the peptide is released with solvent.

Alternatively, the polypeptides can be synthesized by using nucleic acid molecules which encode the peptides of this invention in an appropriate expression vector which include the encoding nucleotide sequences. Such DNA molecules may be readily prepared using an automated DNA sequencer and the well-known codon-amino acid relationship of the genetic code. Such a DNA molecule also may be obtained as genomic DNA or as cDNA using oligonucleotide probes and conventional hybridization methodologies. Such DNA molecules may be incorporated into expression vectors, including plasmids, which are adapted for the expression of the DNA and production of the polypeptide in a suitable host such as bacterium, e.g., *Escherichia coli*, yeast cell or mammalian cell.

It is known that certain modifications can be made without completely abolishing the polypeptide's ability to bind to pleiotrophin or RPTP β/ζ. Modifications include the removal and addition of amino acids. Polypeptides containing other modifications can be synthesized by one skilled in the art and compounds comprising such polypeptides may be tested for biological activity in the various assays and methods described in a later section. Thus, the effectiveness of the polypeptides can be modulated through various changes in the amino acid sequence or structure.

Further, it should be understood that the mimic may be modified using methods known in the art to improve binding, specificity, solubility, safety, or efficacy. A necessary characteristic of these preferred compounds is the capability to interact with pleiotrophin or RPTP β/ζ in such a manner that PTN signaling is disrupted or interfering prevented or inhibited.

The following examples are included to demonstrate preferred embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Example 1

Materials and Methods

Cell Culture

U373-MG glioblastoma (American Type Culture Collection, 10801 University Boulevard, Manassas, Va., 20110-2209, USA) cells were used in all experiments and cultured in DMEM and 10% FCS unless otherwise noted.

Western Blot Analysis

U373-MG glioblastoma cells ($\approx 10^6$) were lysed in 50 mM Tris-HCl (pH 8.0)/150 mM NaCl/1 mM EDTA/1% Triton X-100/1 mM phenylmethylsulfonyl fluoride/0.5 μg/ml leupeptin/1 μM pepstatin/1 μg/ml aprotinin for 30 minutes at 4° C., boiled in SDS/PAGE sample buffer (25 mM Tris-HCl, pH 6.8/2.5% SDS/2.5% glycerol/5% 2-mercaptoethanol), separated by SDS/PAGE, transferred to poly(vinylidenedifluoride) membranes, probed with antibodies as indicated, and illuminated with the enhanced chemiluminescence ECL-PLUS system (Amersham Corp., Arlington Heights, Ill., USA).

Chemical Cross-Linking

U373-MG cells (≈$10^6$) were incubated with the PTN-Fc fragment of IgG (PTN-Fc) for 30 minutes at 37° C., washed with PBS, and incubated with 1 mM of the reversible cross-linking agent 3,3'-dithiobis sulfosuccinimidyl propionate (Pierce Chemical Co., Rockford, Ill., USA) for 30 minutes at 37° C., and lysed.

PTN-Fc "Capture"

U373-MG cells (≈$10^6$) were lysed as above, and proteins associated with PTN-Fc were bound to Protein A Sepharose-4B and, after washing, eluted by boiling in sample buffer and analyzed in Western blots as above.

Glutathione S-Transferase (GST) "Capture" Assays

The GST-juxtamembrane (D1) fragment and the D1 fragment Cys-1925-Ser were prepared by using a human RPTP β/ζ cDNA fragment to encode amino acids 1655–2018 fused with GST in the expression plasmid PGEX-KG XhoI and XbaI sites. The constructs (or GST alone) were expressed in BL-21 competent cells from 5 ml overnight cultures, and the recombinant proteins were immobilized with 100 μl of glutathione-Sepharose-4B beads (Amersham Pharmacia). The beads were then incubated with U373-MG cell lysates from 60-mm confluent dishes, washed, eluted, and analyzed in Western blots as above.

Antibodies and Other Reagents

α-β-catenin and α-RPTP β/ζ antibodies were obtained from Transduction Laboratories (Lexington, Ky.), and α-phosphotyrosine monoclonal antibodies (4G10) were obtained from Upstate Biotechnology (Lake Placid, N.Y., USA). Recombinant PTN was purchased from SIGMA Chemical Company (St. Louis, Mo., USA), and recombinant PTN-Fc was purified from conditioned media of human embryonic kidney 293 cells expressing a cDNA that encodes the full-length PTN molecule fused at its C terminus with the Fc fragment of IgG. For the dose responses of both PTN and PTN-Fc to inactivate RPTP β/ζ, see below. PTN was used at 50 ng/ml and PTN and PTN-Fc were established by using tyrosine phosphorylation of β-catenin and the ability PTN-Fc was used at 5 ng/ml, saturating levels of each, respectively.

Example 2

RPTP β/ζ Tyrosine Phosphatase Activity

PTN-treated U373-MG cells. Confluent U373-MG cells were incubated either with DMEM alone or 50 ng/ml recombinant PTN (Sigma) at 37° C. for 15 minutes, washed three times with PBS, lysed as described above, and cleared at 14,000×g for 15 minutes 4° C. Equal amounts of lysates were incubated with α-RPTP β/ζ antibodies or mouse IgG (control) at 4° C. overnight, incubated with Protein A Sepharose-4B at 4° C. for 2 hours, and washed three times in lysis buffer and once in assay buffer (20 mM imidazole, pH 7.2/0.1 mg/ml BSA). The phosphatase activity of the immobilized RPTP β/ζ protein was assayed as follows: 50 μl of either RPTP β/ζ or mouse IgG immobilized on protein-A beads was added to the assay buffer, the reaction mixture (25 mM imidazole, pH 7.2/0.1 mg/ml BSA/10 mM DTT/100 nM $^{32}$P-labeled substitute Raytide) was added to a final volume of 80 μl, incubated at 30° C. for various times, terminated, and the $^{32}$P released was quantitated by a charcoal-binding assay. The synthetic peptide Raytide (Oncogene Science, Inc., Uniondale, N.Y., USA) was phosphorylated at its unique tyrosine residue by following the manufacturer's instructions.

RPTP β/ζ activity in Sf9 cell membranes. The Bac-to-Bac Baculovirus Expression System (Life Technologies, Gibco/BRL, Gaithersburg, Md., USA) was used to express RPTP β/ζ in Sf9 cells. A full-length human RPTP β/ζ cDNA was cloned into a pFastBac donor plasmid at NotI and XbaI sites (pFastBac-RPTP β/ζ), transformed into DH10Bac *Escherichia coli* which contains bacmid and helper virus, and plasmid DNA prepared. Sf9 cells were infected by the recombinant virus according to the manufacturer's instructions. To prepare membrane fractions, cells were sonicated in a hypotonic lysis buffer (25 mM Tris-HCl, pH 7.5/25 mM sucrose/0.1 mM EDTA/5 mM $MgCl_2$/5 mM DTT/1 mM phenylmethylsulfonyl fluoride/0.5 μg/ml leupeptin/1 μg/ml aprotinin), nuclei were removed by low-speed centrifugation, and membrane fractions were obtained by centrifugation at 100,000×g for 60 minutes at 4° C. The resulting pellets were suspended by sonication in lysis buffer, brought to a concentration of 2 mg/ml, and used to measure PTPase activity as above.

The assays were linear with time and protein concentration.

Example 3

Both Exogenous PTN and the Endogenous Ptn Gene Product Interact with RPTP β/ζ

PTN-Fc was incubated with lysates of serum starved, confluent U373-MG cells, and proteins associated with PTN-FC were captured on Protein A Sepharose and probed by Western blot with anti-(α)-RPTP β/ζ antibodies (FIG. 1B). Three major and other minor alternative-spliced forms of the single RPTP β/ζ gene have been identified (28, 29, 30), and the results of the PTN-FC capture were therefore compared with Western blots of immunoprecipitates from untreated U373-MG cell lysates incubated with A-RPTP β/ζ antibodies (FIG. 1A). Major bands of ≈230, ≈130, ≈85, and variably, in other experiments, ≈250 kDa were identified (FIG. 1A), consistent with the known different spliced forms of RPTP β/ζ previously identified. Depending on the conditions of cell growth, different (presumably alternative-spliced) forms were identified. In Western blots of proteins captured by PTN-Fc from U373-MG cell lysates, two major bands of ≈130 and 85 kDA were identified (FIG. 1B), suggesting that PTN-Fc preferentially associates with isoforms of ≈130 and ≈85 kDa. However, when the blots were exposed for longer times, a faint band at 230 kDa was also seen. When IgG alone was substituted for PTN-Fc, RPTP β/ζ was not captured by Protein A Sepharose (FIG. 1B, left lane). When blots were reprobed with α-IgG antibodies that recognize the Fc portion of PTN-Fc or anti-PTN antibodies, it was established that PTN-Fc was present in the complex captured by Protein A Sepharose.

PTN itself is also expressed in U373-MG cells. To show that the endogenously expressed PTN and RPTP β/ζ interact with each other in vivo, untreated U373-MG cell lysates were immunoprecipitated with α-PTN antibodies and analyzed in Western blots. Anti-RPTP antibodies recognized protein bands at 130 and 85 kDa (faint) (FIG. 1C). These results thus establish that both exogenous and endogenous PTN physically interact with the major alternatively spliced products of RPTP β/ζ in U373-MG cells.

Example 4

PTN Inactivates RPTP β/ζ Activity in vivo and in vitro

Figure 2:
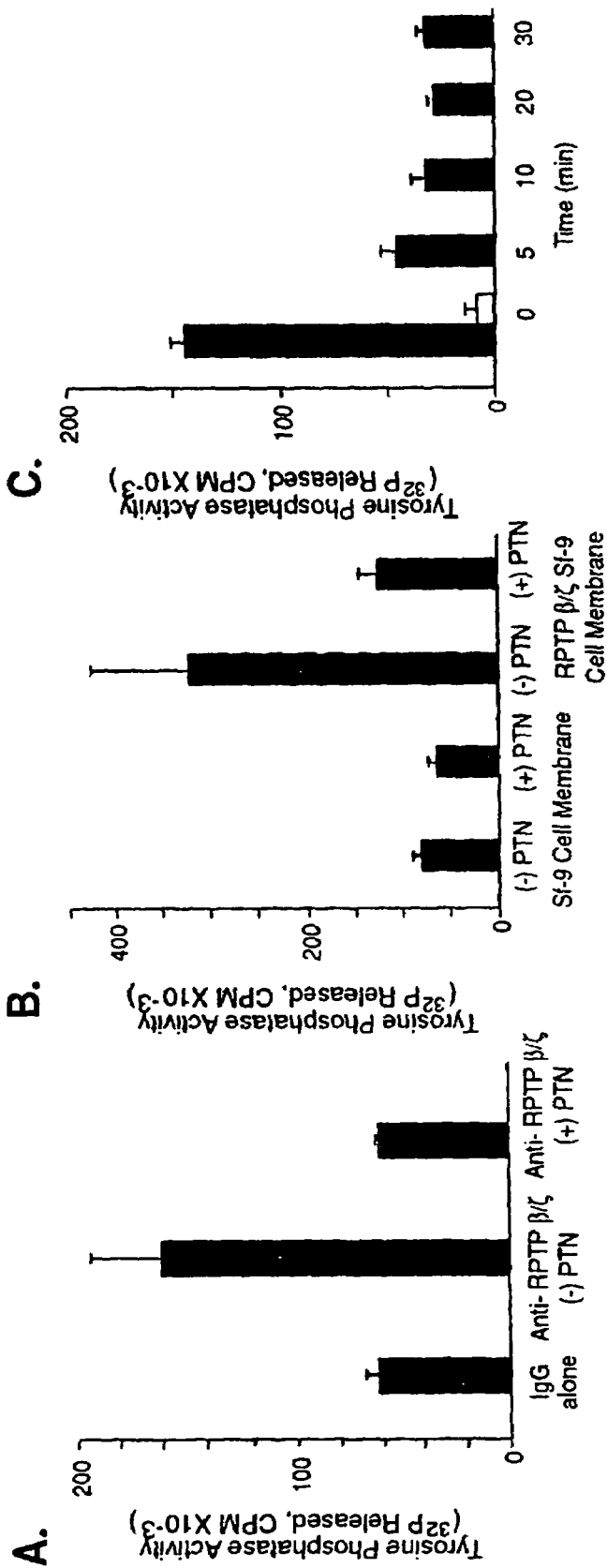
FIGS. 2A, 2B and 2C are a set of three bar charts showing PTN-dependent inhibition of the intrinsic tyrosine phosphatase activity of RPTP β/ζ.

To directly determine if PTN affects the function of endogenous RPTP β/ζ, lysates of PTN-treated and control, untreated U373-MG glioblastoma cells were immunoprecipitated with α-RPTP β/ζ antibodies, incubated with Protein A Sepharose, and directly assayed for protein tyrosine phosphatase activity as described above (FIG. 2A). The effects of PTN on the catalytic activity of recombinant RPTP β/ζ also were tested by using membrane fractions prepared from Sf9 insect cells infected with a baculovirus expressing recombinant RPTP β/ζ. Remarkably, the protein tyrosine phosphatase activity of the endogenous RPTP β/ζ in immunoprecipitates from PTN-treated cells was reduced by more than 90% when compared with RPTP β/ζ from untreated cells and when corrected for non-specific background (IgG controls, FIG. 2A). PTN also strikingly reduced the catalytic activity of recombinant RPTP β/ζ in Sf9 membranes when background phosphatase activity was again corrected (FIG. 2B). The inhibition by PTN is specific, because PTN inhibits tyrosine phosphatase activity only in Sf9 cell membranes that express RPTP β/ζ and the inhibition is rapid (FIG. 2C). Nearly 70% of the phosphatase activity or RPTP β/ζ is lost in 5 minutes. Thus, PTN not only physically associates with RPTP β/ζ but functionally, PTN profoundly reduces the catalytic activity of RPTP β/ζ. Furthermore, because PTN effectively reduces the endogenous RPTP β/ζ activity, it can be concluded that RPTP β/ζ is an intrinsically activity tyrosine phosphatase, thereby suggesting that RPTP β/ζ may be an important regulator of steady-state tyrosine phosphorylation of compatible intracellular substrates that themselves are regulated by an intrinsically active tyrosine kinase activity.

Figure 3:
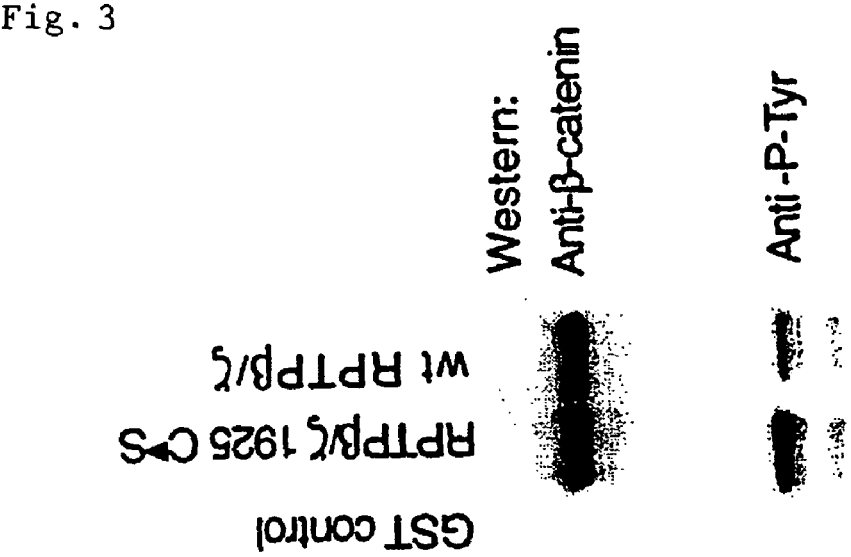
FIGS. 3A and 3B are a set of two (FIG. 3A) and one (FIG. 3B) Western blots, respectively, showing physical and functional association of β-catenin with PTN/RPTP β/ζ.
Figure 3:
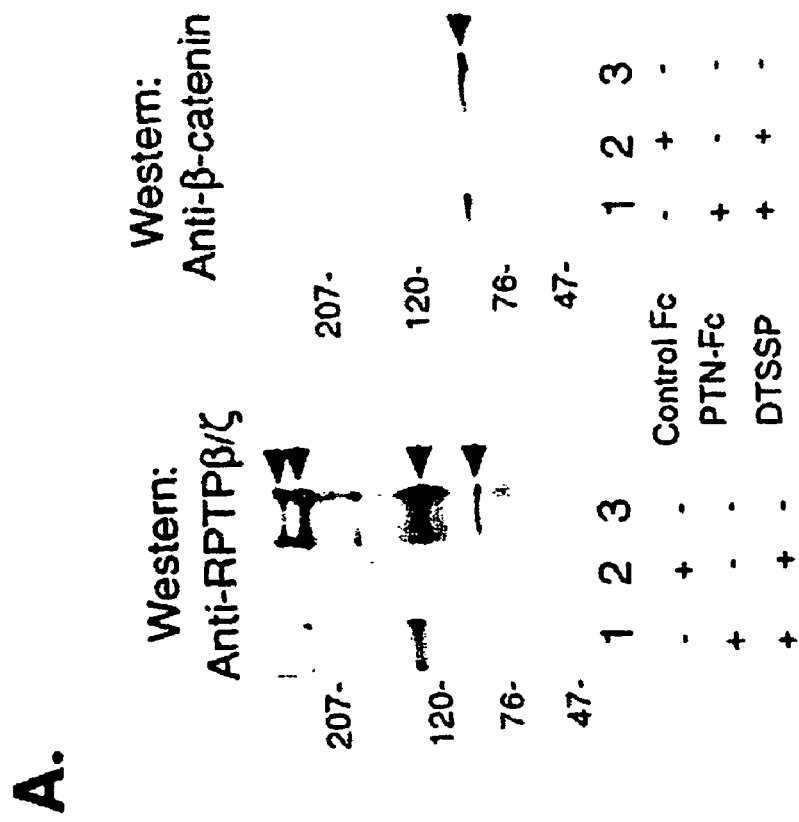

Example 5

β-Catenin is a Potential Substrate for RPTP β/ζ

β-catenin is known to associate with other RPTPs and be phosphorylated in tyrosine (31, 32). β-catenin also is an important signaling molecule in development and in the wnt/APC–/– oncogenic pathways (33, 34, 35), suggesting that its signaling properties may be influenced by tyrosine phosphorylation and potentially be regulated by RPTP β/ζ and/or PTN. PTN-Fc-treated U373-MG cells were therefore incubated with 3,3'-dithiobis-sulfosuccinimidyl-propionate and lysed. Proteins cross-linked to PTN-FC were captured with Protein A Sepharose and analyzed by Western blot with either α-β-catenin (FIG. 3A, right) or α-RPTP β/ζ antibodies (control, FIG. 3A, left). In SDS/PAGE gels, a higher molecular weight complex with very limited migration was identified, and immunoreactive PTN and RPTP β/ζ were identified in this band. In other control experiments, both β-catenin (FIG. 2A Right, lane 3) and RPTP β/ζ (FIG. 3A Left, lane 3) were readily recognized in untreated U373-MG cell lysates. When the captured protein complex from PTN-Fc treated cells cross-linked with 3,3'-dithiobis-sulfosuccinimidyl-propionate was reduced before SDS/PAGE and analyzed in Western blots probed with α-RPTP β/ζ antibodies, RPTP β/ζ-spliced forms of ≈130 kDa, and more weakly, ≈230 kDa, were identified (FIG. 3A, Left, lane 1). These forms were not identified in lysates of cells treated with the Fc fragment of IgG alone (FIG. 3A left, lane 2). Remarkably, PTN-Fc also captured β-catenin, based on recognition by α-β-catenin antibodies and the migration of the band recognized by α-β-catenin antibodies and the migration of the band recognized by α-β-catenin at the estimated molecular mass of β-catenin (≈94 kDa) (FIG. 3A Right lane 1). β-catenin was not captured when cells were treated with the Fc fragment of IgG alone (FIG. 3A Right, lane 2). The results confirm that the extracellular domain of RPTP β/ζ interacts with PTN-Fc and suggest that β-catenin interacts with its intracellular domain. These results also raise the possibility that RPTP β/ζ links PTN signaling to β-catenin.

RPTP β/ζ has two phosphatase domains in its C-terminal cytoplasmic tail. The juxtamembrane-proximal D1 domain of RPTP β/ζ contains an active tyrosine phosphatase catalytic unit whereas the juxtamembrane-distal D2 domain lacks the required cysteine residue and thus is inactive (36). To see whether β-catenin associates with the active site of RPTP β/ζ, the D1 domain and the D1 domain Cys-1925-Ser (active site inactivating) mutation were coupled with GST, incubated for 15 minutes with U373-MG cell lysates from cells pretreated with pervanidate, and analyzed in Western blots. Both the active and inactive D1 domains of RPTP β/ζ β-catenin (FIG. 3B, upper) at essentially equal levels. However, when the Western blots were reprobed with α-phosphotyrosine antibodies, the levels of tyrosine phosphorylation of β-catenin were sharply reduced in lysates incubated with the active (wt) D1 domain compared with the D1 domain Cys-1925-Ser (FIG. 3B, lower), localizing the association of β-catenin to the active site-containing D1 domain and strongly suggesting that β-catenin is a substrate of RPTP β/ζ.

Example 6

PTN Stimulates Tyrosine Phosphorylation of β-Catenin

Figure 4:
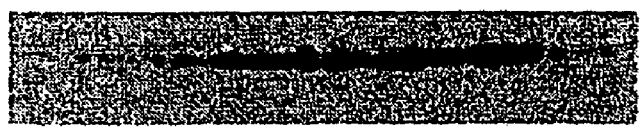
FIGS. 4A and 4B are a pair of western blots showing increased β-catenin tyrosine phosphorylation.
Figure 4:
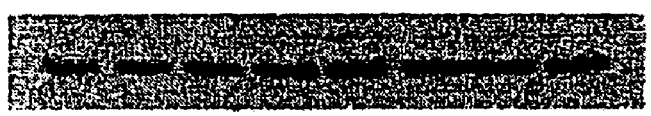
Figure 4:

To pursue the possibility that β-catenin is a substrate of RPTP β/ζ in intact cells and that PTN-dependent inactivation of RPTP β/ζ influences tyrosine phosphorylation of β-catenin, tyrosine phosphorylation was examined temporally after the addition of PTN-Fc to intact U373-MG cells. Tyrosine phosphorylation of β-catenin increased within 2 minutes of addition of PTN and reached peak levels within 8 minutes (FIG. 4A). The levels of β-catenin itself were essentially identical, indicating that PTN-Fc had no detectable influence on the levels of β-catenin protein. Furthermore, the response was PTN-Fc dose-dependent between 0.2 and 5 ng/ml (FIG. 4B).

All references, patents and patent applications are incorporated herein by reference in their entirety. While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method of reducing levels of tyrosine phosphatase activity of protein tyrosine phosphataseζ/receptor-like protein tyrosine phosphatase β (RPTP β/ζ) in a mammalian cell in vitro that expresses RPTP β/ζ, the method comprising administering to the cell in vitro a mammalian pleiotrophin of about 18 kDa in an amount effective to reduce the tyrosine phosphatase activity of the RPTP β/ζ.

2. A method of increasing tyrosine phosphorylation of β-catenin in a mammalian cell that expresses RPTP β/ζ, said method comprising contacting the cell that expresses the RPTP β/ζ with a mammalian pleiotrophin of about 18 kDa in vitro in an amount effective for reducing tyrosine phosphatase activity of the RPTP β/ζ, thereby increasing tyrosine phosphorylation of the β-catenin.

3. The method of claim 3, wherein the amount of the mammalian pleiotrophin effective for reducing tyrosine phosphatase activity of the RPTP β/ζ is an amount of the pleiotrophin effective for inducing ligand-dependent dimerization of the RPTP β/ζ.

4. The method of claim 3 wherein the amount of the mammalian pleiotrophin effective for inducing ligand-dependent dimerization of the RPTP β/ζ is an amount of the pleiotrophin effective for inhibiting the ability of the β-catenin to bind to the catalytic site of the RPTP β/ζ.

5. The method of claim 4 wherein the catalytic site of the RPTP β/ζ is the D1 domain of the RPTP β/ζ.

6. The method of claim 1, wherein the mammalian pleiotrophin is selected from the group consisting of a bovine pleiotrophin, a human pleiotrophin, a rat pleiotrophin and a mouse pleiotrophin.

7. The method of claim 1, wherein the mammalian pleiotrophin is a human pleiotrophin.

* * * * *